US012214117B2

(12) United States Patent
Jones et al.

(10) Patent No.: US 12,214,117 B2
(45) Date of Patent: Feb. 4, 2025

(54) AUTOMATED URINARY OUTPUT MONITORING SYSTEM

(71) Applicant: C. R. Bard, Inc., Franklin Lakes, NJ (US)

(72) Inventors: Jill Walthall Jones, Avondale Estates, GA (US); Eric A. Fallows, Apex, NC (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 0 days.

(21) Appl. No.: 17/902,705

(22) Filed: Sep. 2, 2022

(65) Prior Publication Data

US 2023/0083906 A1 Mar. 16, 2023

Related U.S. Application Data

(60) Provisional application No. 63/242,986, filed on Sep. 10, 2021.

(51) Int. Cl.
*A61M 1/00* (2006.01)
*A61B 5/20* (2006.01)
(Continued)

(52) U.S. Cl.
CPC ............... *A61M 1/85* (2021.05); *A61B 5/208* (2013.01); *A61F 5/4405* (2013.01); *A61M 25/0043* (2013.01); *A61M 2209/082* (2013.01)

(58) Field of Classification Search
CPC ............... A61M 1/85; A61M 25/0043; A61M 2202/0496; A61M 2209/082;
(Continued)

(56) References Cited

U.S. PATENT DOCUMENTS 3,114,916 A    12/1963   Hadley
3,583,401 A     6/1971   Vailiancourt et al.
(Continued)

FOREIGN PATENT DOCUMENTS

EP    1872752 A1    1/2008
EP    2417955 A2    2/2012
(Continued)

OTHER PUBLICATIONS

PCT/US2020/066707 filed Dec. 22, 2020 International Search Report and Written Opinion dated Apr. 15, 2021.
(Continued)

*Primary Examiner* — Leslie A Lopez
*Assistant Examiner* — Timothy L Flynn
(74) *Attorney, Agent, or Firm* — Rutan & Tucker LLP

(57) ABSTRACT

Disclosed herein is an automated urinary output monitoring system including urine collection assembly that includes a first drainage tube coupled between a urinary catheter and an interim container, and a second drainage coupled between the interim container and a final container. A scale measures the weight of urine collected in the final container and a display depicts the volume of urine collected in the final container. A vacuum pump can be coupled with the final container to draw urine from the interim container into the final container, and an air vent can isolate the patient from the vacuum within the final container. The system can be configured to wirelessly transmit urine volume data to an external computing device. A gyroscope can be coupled with the scale to determine the orientation of the scale. Logic of the system can calculate urine volume and correlate with the time of day.

26 Claims, 9 Drawing Sheets

(51) Int. Cl.
*A61F 5/44* (2006.01)
*A61M 25/00* (2006.01)

(58) Field of Classification Search
CPC .... A61M 2205/3393; A61M 2205/502; A61M 1/72; A61M 1/73; A61B 5/204; A61B 5/205; A61B 5/207; A61B 5/208; A61B 2505/03; A61B 2505/07; A61B 5/201; A61B 5/14507; A61B 5/14539; A61B 10/007; A61F 5/4405; B65B 69/0016; B65B 59/0093; B65B 69/0091
See application file for complete search history.

(56) References Cited

U.S. PATENT DOCUMENTS

| | | |
|---|---|---|
| 3,598,124 A | 8/1971 | Andersen et al. |
| 3,661,143 A | 5/1972 | Henkin |
| 3,861,394 A | 1/1975 | Villari |
| 3,901,235 A | 8/1975 | Patel et al. |
| 3,955,574 A | 5/1976 | Rubinstein |
| 4,084,593 A | 4/1978 | Jarund |
| 4,265,243 A | 5/1981 | Taylor |
| 4,305,403 A | 12/1981 | Dunn |
| 4,315,506 A | 2/1982 | Kayser et al. |
| 4,360,933 A | 11/1982 | Kimura et al. |
| 4,465,485 A | 8/1984 | Kashmer et al. |
| 4,490,144 A | 12/1984 | Steigerwald |
| 4,531,939 A | 7/1985 | Izumi |
| 4,631,061 A | 12/1986 | Martin |
| 4,654,029 A | 3/1987 | D'Antonio |
| 4,747,166 A | 5/1988 | Kuntz |
| 4,819,684 A | 4/1989 | Zaugg et al. |
| 4,872,579 A | 10/1989 | Palmer |
| 4,990,137 A | 2/1991 | Graham |
| 5,002,528 A | 3/1991 | Palestrant |
| 5,071,411 A | 12/1991 | Hillstead |
| 5,186,431 A | 2/1993 | Tamari |
| 5,318,550 A | 6/1994 | Cermak et al. |
| 5,405,319 A | 4/1995 | Abell et al. |
| 5,738,656 A | 4/1998 | Wagner et al. |
| 5,813,842 A | 9/1998 | Tamari |
| 5,894,608 A | 4/1999 | Birbara |
| 6,007,521 A | 12/1999 | Bidwell et al. |
| 6,106,506 A | 8/2000 | Abell et al. |
| 6,183,454 B1 | 2/2001 | Levine et al. |
| 8,266,741 B2 | 9/2012 | Penninger et al. |
| 8,337,475 B2 | 12/2012 | Christensen et al. |
| 8,475,419 B2 | 7/2013 | Eckermann |
| 8,512,301 B2 | 8/2013 | Ma |
| 10,391,275 B2 | 8/2019 | Burnett et al. |
| 10,426,919 B2 | 10/2019 | Erbey, II et al. |
| 10,506,965 B2 | 12/2019 | Cooper et al. |
| 10,737,057 B1 | 8/2020 | Mikhail et al. |
| 10,772,998 B2 | 9/2020 | Luxon et al. |
| 2002/0000253 A1 | 1/2002 | Fillmore et al. |
| 2002/0161317 A1 | 10/2002 | Risk et al. |
| 2003/0078638 A1 | 4/2003 | Voorhees et al. |
| 2004/0176746 A1 | 9/2004 | Forral |
| 2004/0230181 A1 | 11/2004 | Cawood |
| 2004/0236292 A1 | 11/2004 | Tazoe et al. |
| 2004/0254547 A1 | 12/2004 | Okabe et al. |
| 2005/0209585 A1 | 9/2005 | Nord et al. |
| 2005/0245898 A1 | 11/2005 | Wright et al. |
| 2005/0261619 A1 | 11/2005 | Gay |
| 2006/0015190 A1 | 1/2006 | Robertson |
| 2006/0079854 A1 | 4/2006 | Kay et al. |
| 2006/0155260 A1 | 7/2006 | Blott et al. |
| 2006/0235353 A1 | 10/2006 | Gelfand et al. |
| 2006/0270971 A1* | 11/2006 | Gelfand ............... A61M 5/1723 604/151 |
| 2006/0271019 A1 | 11/2006 | Stoller et al. |
| 2007/0078444 A1 | 4/2007 | Larsson |
| 2007/0142729 A1 | 6/2007 | Pfeiffer et al. |
| 2007/0272311 A1 | 11/2007 | Trocki et al. |
| 2008/0156092 A1 | 7/2008 | Boiarski |
| 2009/0157016 A1 | 6/2009 | Adahan |
| 2009/0157040 A1 | 6/2009 | Jacobson et al. |
| 2009/0326483 A1 | 12/2009 | Green |
| 2010/0106116 A1 | 4/2010 | Simmons et al. |
| 2010/0130949 A1 | 5/2010 | Garcia |
| 2011/0060300 A1 | 3/2011 | Weig et al. |
| 2012/0036638 A1 | 2/2012 | Penninger et al. |
| 2012/0323144 A1 | 12/2012 | Coston et al. |
| 2013/0218106 A1 | 8/2013 | Coston et al. |
| 2014/0200558 A1 | 7/2014 | McDaniel |
| 2015/0126975 A1 | 5/2015 | Wuthier |
| 2015/0290448 A1 | 10/2015 | Pavlik |
| 2016/0135982 A1 | 5/2016 | Garcia |
| 2016/0183819 A1 | 6/2016 | Burnett et al. |
| 2016/0310711 A1 | 10/2016 | Luxon et al. |
| 2017/0072125 A1 | 3/2017 | Wallenås et al. |
| 2017/0136209 A1 | 5/2017 | Burnett et al. |
| 2017/0143566 A1 | 5/2017 | Elku et al. |
| 2017/0241978 A1 | 8/2017 | Duval |
| 2017/0312114 A1 | 11/2017 | Glithero |
| 2018/0015251 A1 | 1/2018 | Lampotang et al. |
| 2018/0071441 A1 | 3/2018 | Croteau et al. |
| 2018/0104391 A1 | 4/2018 | Luxon et al. |
| 2018/0110456 A1 | 4/2018 | Cooper et al. |
| 2018/0125697 A1 | 5/2018 | Ferrera |
| 2018/0177458 A1 | 6/2018 | Burnett et al. |
| 2018/0235523 A1 | 8/2018 | Sauder |
| 2018/0245699 A1 | 8/2018 | Lee |
| 2018/0360424 A1 | 12/2018 | Yurek et al. |
| 2019/0009021 A1 | 1/2019 | Nelson et al. |
| 2019/0009023 A1 | 1/2019 | Diperna et al. |
| 2019/0038451 A1 | 2/2019 | Harvie |
| 2019/0046102 A1 | 2/2019 | Kushnir et al. |
| 2019/0126006 A1 | 5/2019 | Rehm et al. |
| 2019/0143094 A1 | 5/2019 | DeMeritt |
| 2019/0151610 A1 | 5/2019 | Fletter |
| 2019/0343445 A1 | 11/2019 | Burnett et al. |
| 2020/0000979 A1 | 1/2020 | Myers |
| 2020/0061281 A1 | 2/2020 | Desouza et al. |
| 2020/0315837 A1 | 10/2020 | Radl et al. |
| 2021/0077007 A1* | 3/2021 | Jouret ................... A61B 5/0002 |
| 2022/0152345 A1 | 5/2022 | Simiele et al. |
| 2022/0160949 A1 | 5/2022 | Simiele et al. |
| 2022/0176031 A1 | 6/2022 | Cheng et al. |
| 2022/0193366 A1 | 6/2022 | Cheng et al. |
| 2022/0218890 A1 | 7/2022 | Chavan |
| 2022/0218973 A1 | 7/2022 | Chavan et al. |
| 2022/0218974 A1 | 7/2022 | Chavan et al. |
| 2022/0273213 A1* | 9/2022 | Sokolov ............ A61B 5/02055 |
| 2022/0305189 A1 | 9/2022 | Chavan et al. |
| 2022/0330867 A1* | 10/2022 | Conley ............... A61M 5/1723 |
| 2022/0362080 A1* | 11/2022 | McCorquodale .... A61G 7/0507 |
| 2022/0409421 A1 | 12/2022 | Hughett et al. |
| 2023/0013353 A1 | 1/2023 | Chavan et al. |
| 2023/0030637 A1 | 2/2023 | Gloeckner et al. |
| 2023/0054937 A1 | 2/2023 | Chancy et al. |
| 2023/0310837 A1* | 10/2023 | Gamsizlar ............ A61B 90/50 604/6.11 |
| 2024/0238500 A1 | 7/2024 | Simiele et al. |
| 2024/0307604 A1 | 9/2024 | Chavan |

FOREIGN PATENT DOCUMENTS

| | | |
|---|---|---|
| EP | 2730299 A1 | 5/2014 |
| WO | 2009/026237 A1 | 2/2009 |
| WO | 2012016179 A1 | 2/2012 |
| WO | 2015019056 A1 | 2/2015 |
| WO | 2015/105916 A1 | 7/2015 |
| WO | 2016012494 A1 | 1/2016 |
| WO | 2017177068 A1 | 10/2017 |
| WO | 2018136306 A1 | 7/2018 |
| WO | 2018191193 A1 | 10/2018 |
| WO | 2019004854 A1 | 1/2019 |
| WO | 2020033752 A1 | 2/2020 |
| WO | 2021154427 A1 | 8/2021 |
| WO | 2022/159333 A1 | 7/2022 |

(56) References Cited

FOREIGN PATENT DOCUMENTS

WO   2022/251425 A1   12/2022
WO   2023086394 A1   5/2023

OTHER PUBLICATIONS

PCT/US2022/012373 filed Jan. 13, 2022 International Search Report and Written Opinion dated Apr. 19, 2022.
PCT/US2022/049418 filed Nov. 9, 2022 International Search Report and Written Opinion dated Feb. 10, 2023.
U.S. Appl. No. 17/526,994, filed Nov. 15, 2021 Restriction Requirement dated Jan. 3, 2023.
U.S. Appl. No. 17/556,942, filed Dec. 20, 2021 Non-Final Office Action dated Jan. 31, 2023.
U.S. Appl. No. 17/561,504, filed Dec. 23, 2021 Non-Final Office Action dated Mar. 14, 2023.
U.S. Appl. No. 17/526,994, filed Nov. 15, 2021 Non-Final Office Action dated May 10, 2023.
U.S. Appl. No. 17/532,454, filed Nov. 22, 2021 Non-Final Office Action dated Mar. 22, 2023.
U.S. Appl. No. 17/542,060, filed Dec. 3, 2021 Non-Final Office Action dated Jun. 27, 2023.
U.S. Appl. No. 17/556,942, filed Dec. 20, 2021 Final Office Action dated Jul. 12, 2023.
U.S. Appl. No. 17/561,458, filed Dec. 23, 2021 Non-Final Office Action dated Jun. 16, 2023.
U.S. Appl. No. 17/561,504, filed Dec. 23, 2021 Final Office Action dated Jul. 19, 2023.
U.S. Appl. No. 17/863,898, filed Jul. 13, 2022 Non-Final Office Action dated Jul. 17, 2023.
U.S. Appl. No. 17/373,568, filed Jul. 12, 2021 Non-Final Office Action dated Nov. 9, 2023.
U.S. Appl. No. 17/526,994, filed Nov. 15, 2021 Final Office Action dated Oct. 24, 2023.
U.S. Appl. No. 17/532,454, filed Nov. 22, 2021 Final Office Action dated Sep. 27, 2023.
U.S. Appl. No. 17/556,942, filed Dec. 20, 2021 Advisory Action dated Sep. 1, 2023.
U.S. Appl. No. 17/556,942, filed Dec. 20, 2021 Non-Final Office Action dated Nov. 3, 2023.
U.S. Appl. No. 17/561,458, filed Dec. 23, 2021 Final Office Action dated Sep. 12, 2023.
U.S. Appl. No. 17/526,994, filed Nov. 15, 2021 Advisory Action dated Jan. 19, 2024.
U.S. Appl. No. 17/532,454, filed Nov. 22, 2021 Notice of Allowance dated Dec. 8, 2023.
U.S. Appl. No. 17/542,060, filed Dec. 3, 2021 Non-Final Office Action dated Nov. 28, 2023.
U.S. Appl. No. 17/561,458, filed Dec. 23, 2021 Notice of Allowance dated Dec. 6, 2023.
U.S. Appl. No. 17/561,504, filed Dec. 23, 2021 Non-Final Office Action dated Nov. 27, 2023.
U.S. Appl. No. 17/561,504, filed Dec. 23, 2021 Notice of Allowance dated Jan. 22, 2024.
U.S. Appl. No. 17/863,898, filed Jul. 13, 2022 Advisory Action dated Jan. 30, 2024.
U.S. Appl. No. 17/863,898, filed Jul. 13, 2022 Final Office Action dated Nov. 22, 2023.
U.S. Appl. No. 17/542,060, filed Dec. 3, 2021 Notice of Allowance dated Jun. 3, 2024.
U.S. Appl. No. 17/556,942, filed Dec. 20, 2021 Notice of Allowance dated Jun. 26, 2024.
U.S. Appl. No. 17/373,568, filed Jul. 12, 2021 Notice of Allowance dated Apr. 26, 2024.
U.S. Appl. No. 17/526,994, filed Nov. 15, 2021 Non-Final Office Action dated Apr. 22, 2024.
U.S. Appl. No. 17/556,942, filed Dec. 20, 2021 Final Office Action dated Apr. 4, 2024.
U.S. Appl. No. 17/796,604, filed Jul. 29, 2022 Notice of Allowance dated May 1, 2024.
U.S. Appl. No. 17/863,898, filed Jul. 13, 2022 Non-Final Office Action dated Mar. 11, 2024.
U.S. Appl. No. 17/571,254, filed Jan. 7, 2022 Restriction Requirement dated Oct. 4, 2024.
U.S. Appl. No. 17/863,898, filed Jul. 13, 2022 Final Office Action dated Aug. 22, 2024.

* cited by examiner

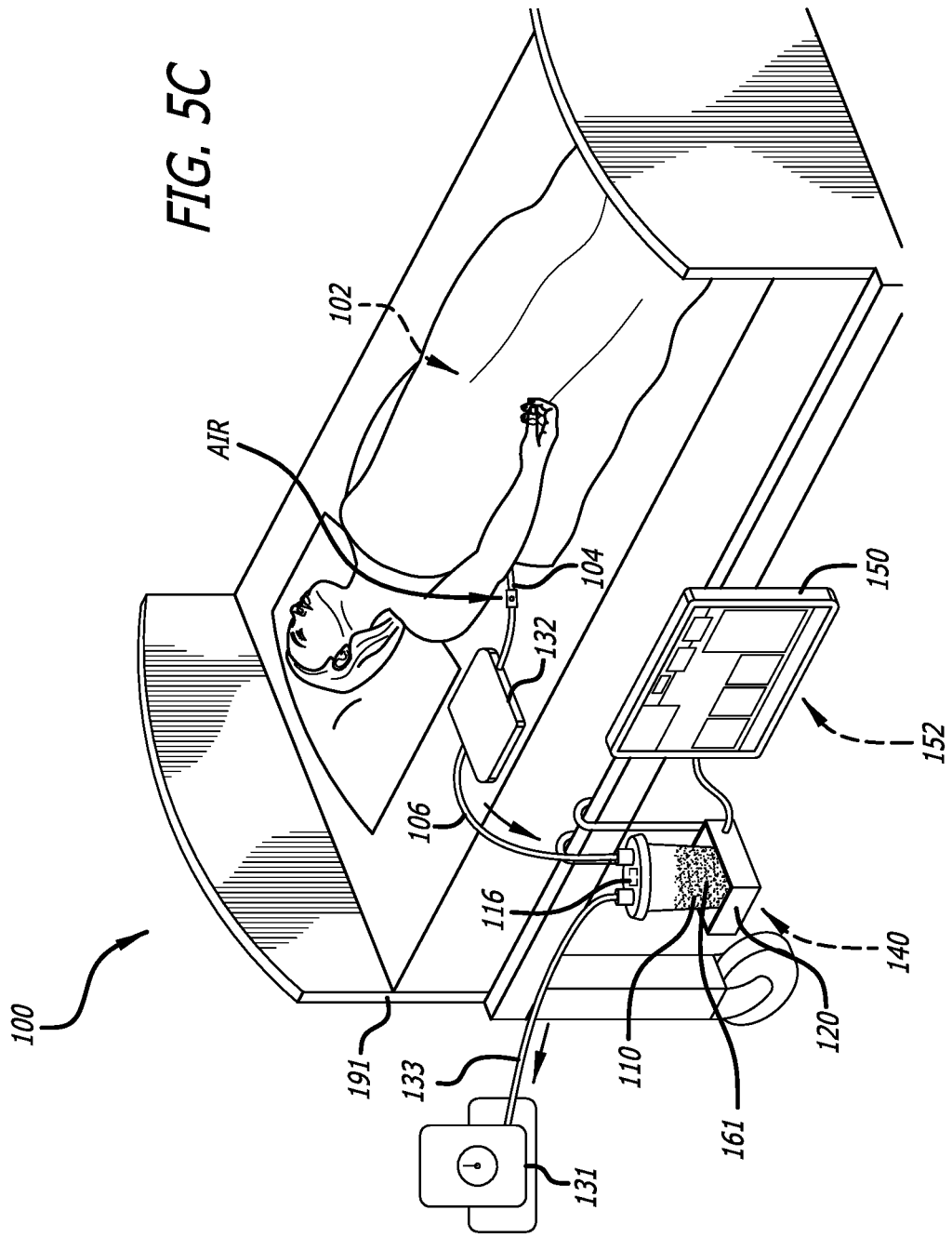

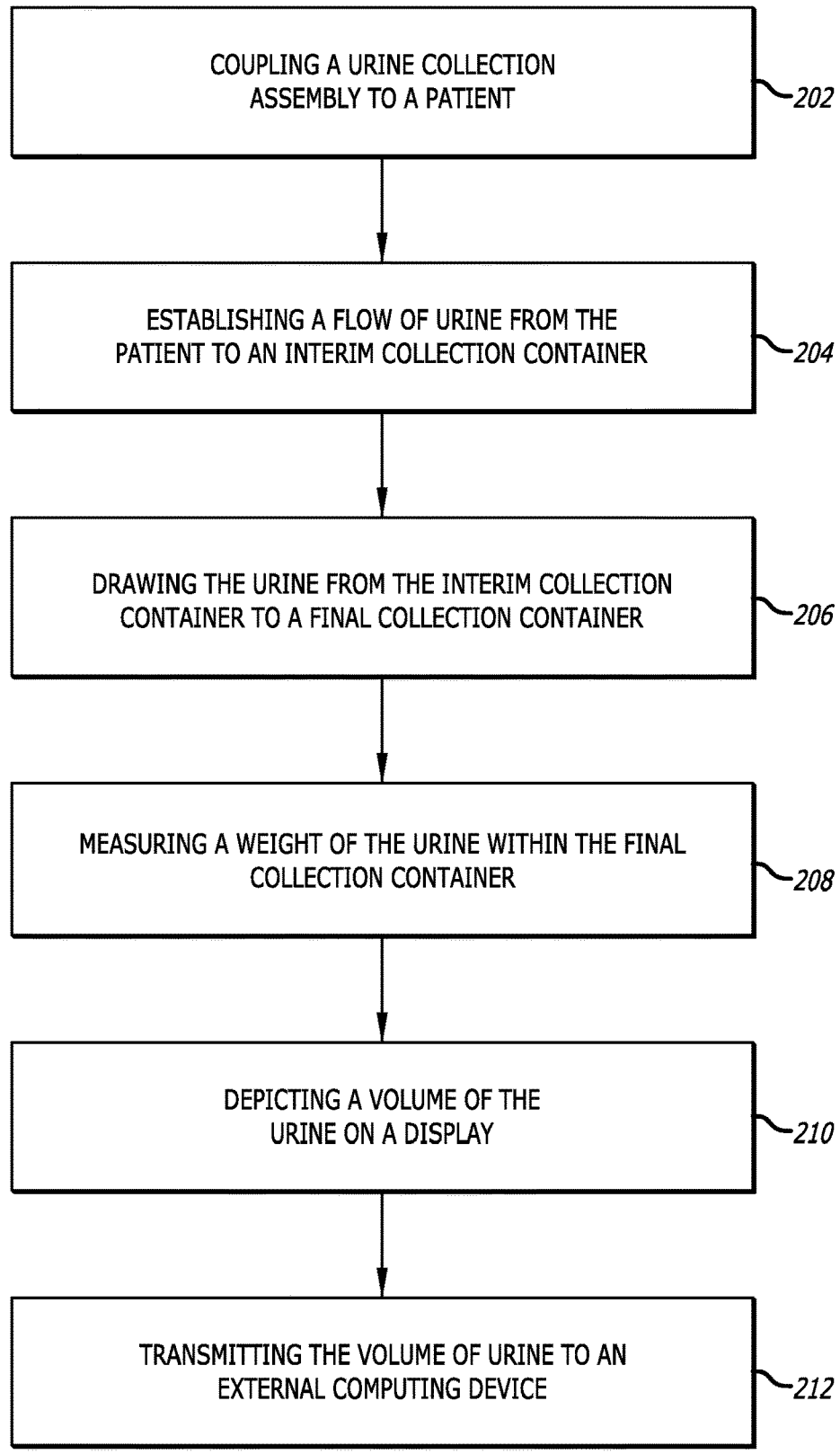

AUTOMATED URINARY OUTPUT MONITORING SYSTEM

PRIORITY

This application claims the benefit of priority to U.S. Provisional Application No. 63/242,986, filed Sep. 10, 2021, which is incorporated by reference in its entirety into this application.

BACKGROUND

Some current urine monitoring systems use weight based methodologies to determine urine volume and urine flow rate over time. A fluid collection container may be suspended from a weighing device and as urine is captured by the fluid collection container by gravity flow, the weight of the fluid collection container increases. The weighing device may be configured to detect the increase in the weight of the fluid collection container. However, the weight of the fluid collection container and the weighing device may make it challenging for nurses to lift and transport. Furthermore, the weighing device can be bulky, taking up valuable floor space in a patient's room and residual urine may be left within patient tubing. It would be beneficial to clinician and the patient to have a urine monitoring system that does not take up valuable space in the patient's room and is able to accurately measure the entire volume of urine voided by the patient. Disclosed herein is an automated urinary output monitoring system and method of use that addresses the foregoing.

SUMMARY

Disclosed herein is an automated urinary output monitoring system that, according to some embodiments, includes a urine collection assembly having an interim collection container configured to fluidly couple with a urinary catheter via a first drainage tube, where the first drainage tube defines a lumen extending along a length of the first drainage tube, and a final collection container fluidly coupled with the interim collection container via a second drainage tube. The system further includes a scale configured to determine a weight of urine collected within the final collection container and a pump configured to cause urine to flow from the interim collection container to the final collection container via the second drainage tube. In some embodiments, the urine collection assembly includes the urinary catheter coupled with the first drainage tube.

In some embodiments, the pump is fluidly coupled with the final collection container via an air hose, and in some embodiments, the pump is configured to generate vacuum within the final collection container.

In some embodiments, the urine collection assembly includes air vent coupled with the first drainage tube, where the air vent is configured to enable air to flow from the environment into the lumen. In some embodiments, the air vent is configured to prevent urine from flowing from the lumen to the environment. In some embodiments, the air vent includes a filter disposed in line with the air vent, where the filter is configured to prevent microbial contaminates from entering the lumen via the air vent.

In some embodiments, the first drainage tube includes a one-way valve disposed in line with the first drainage tube, where the one way valve is configured to prevent fluid flow along the first drainage tube toward the urinary catheter.

In some embodiments, the system further includes a frame coupled with the scale, where the frame is configured to secure the scale to a bed. In some embodiments, the frame includes one or more hooks configured to suspend the frame from a rail of the bed.

In some embodiments, the system further includes a system module operatively coupled with the scale and a display, where the system module includes a console that includes a number of processors and a non-transitory computer readable medium having logic stored thereon that, when executed by the processors performs system operations that include (i) receiving weight data from the scale (ii) calculating a volume of urine contained with the final collection container based on the weight data, and (iii) depicting the volume of urine on the display.

In some embodiments, the final container includes a pressure sensor, and the system operations further include receiving pressure data from the pressure sensor and at least one of (i) determining a depth of the urine contained within the final collection container based on the pressure data and calculating the volume of urine based on the depth or (ii) detecting a vacuum within the final collection container.

In some embodiments, the system operations further include transmitting the volume of the urine contained with the final collection container to at least one of (i) an electronic medical record system or (ii) an external computing device.

In some embodiments, the scale includes a scale console that includes a number of processors and a non-transitory computer readable medium having scale logic stored thereon that, when executed by the processors performs scale operations, including at least one of (i) transmitting weight data to the system module via wired connection or (ii) wirelessly transmitting weight data to the system module.

In some embodiments, the scale includes a gyroscope, and the scale operations further include receiving gyroscope data from the gyroscope, determining an orientation of the scale based on the gyroscope data, and at least one of (i) communicating the orientation of the scale to the system module for depiction on the display or (ii) applying a correction factor to weight data based on the orientation of the scale.

Also disclosed herein is a method of measuring (or otherwise determining) a volume of urine output from a patient that, according to some embodiments, includes (i) receiving urine from a urinary catheter via a first drainage tube, where the first drainage tube extends between the urinary catheter and an interim collection container; (ii) collecting the urine within the interim collection container; (iii) drawing air into the first drainage tube via an air vent of the first drainage tube, where a pressure of the air transports the urine from the interim collection container to a final collection container; (iv) determining a weight of the urine within the final collection container; and (v) calculating a volume of the urine within the final collection container based on the weight.

In some embodiments, drawing air into the first drainage tube includes generating a vacuum within the final collection container.

In some embodiments, collecting the urine within the interim collection container includes collecting a first amount of urine and collecting a second amount of urine subsequent to collecting the first amount of urine, and drawing air into the first drainage tube includes (i) activating a vacuum pump coupled with the final collection container for a first activation time period to transport the first amount of urine from the interim collection container to the final collection container, (ii) deactivating the vacuum pump for a defined deactivation time period after the first activation time period, and (iii) activating the vacuum pump for a second activation time period to transport the second amount of urine from the interim collection container to the final collection container.

In some embodiments, determining a weight of the urine within the final collection container includes determining a weight of the first amount of urine and determining a weight of the second amount of urine.

In some embodiments, the method further includes determining a rate of urine output based on the weight of the second amount of urine and the defined deactivation time period.

These and other features of the concepts provided herein will become more apparent to those of skill in the art in view of the accompanying drawings and following description, which describe particular embodiments of such concepts in greater detail.

DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIGS. 5A-5C illustrate the system of FIG. 1 in various states of a urine output monitoring process, in accordance with some embodiments; and FIG. 6 illustrates a flow chart of an exemplary method of monitoring urine output from a patient, in accordance with some embodiments.

DESCRIPTION

Figure 1:
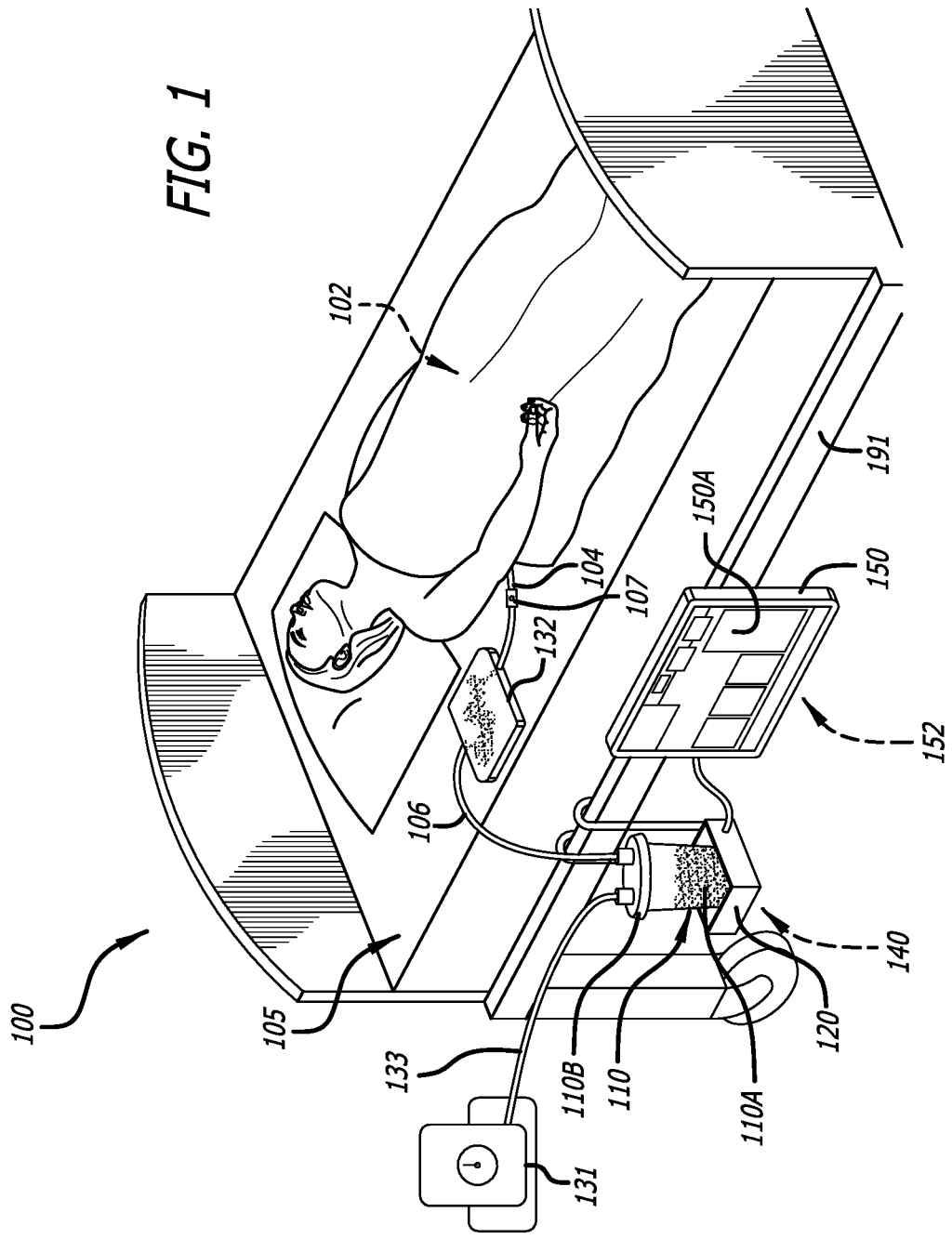
FIG. 1 illustrates a perspective view of an automated urinary output monitoring system including a urine collection assembly, in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal-end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal-end portion, or the proximal length of the catheter can include the proximal end of the catheter; however, the proximal portion, the proximal-end portion, or the proximal length of the catheter need not include the proximal end of the catheter. That is, unless context suggests otherwise, the proximal portion, the proximal-end portion, or the proximal length of the catheter is not a terminal portion or terminal length of the catheter.

With respect to "distal," a "distal portion" or a "distal-end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal-end portion, or the distal length of the catheter can include the distal end of the catheter; however, the distal portion, the distal-end portion, or the distal length of the catheter need not include the distal end of the catheter. That is, unless context suggests otherwise, the distal portion, the distal-end portion, or the distal length of the catheter is not a terminal portion or terminal length of the catheter.

The term "logic" may be representative of hardware, firmware or software that is configured to perform one or more functions. As hardware, the term logic may refer to or include circuitry having data processing and/or storage functionality. Examples of such circuitry may include, but are not limited or restricted to a hardware processor (e.g., microprocessor, one or more processor cores, a digital signal processor, a programmable gate array, a microcontroller, an application specific integrated circuit "ASIC", etc.), a semiconductor memory, or combinatorial elements.

Additionally, or in the alternative, the term logic may refer to or include software such as one or more processes, one or more instances, Application Programming Interface(s) (API), subroutine(s), function(s), applet(s), servlet(s), routine(s), source code, object code, shared library/dynamic link library (dll), or even one or more instructions. This software may be stored in any type of a suitable non-transitory storage medium, or transitory storage medium (e.g., electrical, optical, acoustical or other form of propagated signals such as carrier waves, infrared signals, or digital signals). Examples of a non-transitory storage medium may include, but are not limited or restricted to a programmable circuit; non-persistent storage such as volatile memory (e.g., any type of random access memory "RAM"); or persistent storage such as non-volatile memory (e.g., read-only memory "ROM", power-backed RAM, flash memory, phase-change memory, etc.), a solid-state drive, hard disk drive, an optical disc drive, or a portable memory device. As firmware, the logic may be stored in persistent storage.

The term "computing device" should be construed as electronics with a data processing capability and/or a capability of connecting to any type of network, such as a public network (e.g., Internet), a private network (e.g., a wireless data telecommunication network, a local area network "LAN", etc.), or a combination of networks. Examples of a computing device may include, but are not limited or restricted to, the following: a server, an endpoint device (e.g., a laptop, a smartphone, a tablet, a "wearable" device such as a smart watch, augmented or virtual reality viewer, or the like, a desktop computer, a netbook, a medical device, or any general-purpose or special-purpose, user-controlled electronic device), a mainframe, internet server, a router; or the like.

The phrases "connected to," "coupled to/with," and "in communication with" refer to any form of interaction between two or more entities, including but not limited to mechanical, electrical, magnetic, electromagnetic, fluid, and thermal interaction. Two components may be coupled to each other even though they are not in direct contact with each other. For example, two components may be coupled to each other through an intermediate component.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Unless defined otherwise, all technical and scientific terms used herein have the same meaning as commonly understood by those of ordinary skill in the art.

FIG. 1 illustrates a perspective view of an automated urinary output monitoring system (system) 100, in accordance with some embodiments. The system 100 is generally configured to collect and determine/monitor urine output (i.e., volume of urine) from a patient. The system 100 generally includes a urine collection assembly 105, a scale 140, a system module (module) 150, and a vacuum pump (pump) 131. The urine collection assembly (assembly) 105 includes a fluid components configured to (i) provide a flow path for urine to flow proximally away from the patient and (ii) collect the urine within a container. The scale 140 is generally configured to determine a weight urine collected within the container and communicate the weight to the system module 150 which depicts information pertaining to the weight or volume of the urine collected in the container on a display 150A of the module 150. The pump 131 is generally configured to urge the urine to flow from the patient to the collection container. The scale 131, the system module 150 and the pump 131 are capital equipment configured for reuse across patients. The urine collection assembly 105 is generally configured for single use, such as use with a single patient, for example. Detailed description of the assembly 105, the scale 140, the module 150 and the pump 131 follows below.

The assembly 105 includes a final collection container (container) 110 at a proximal end of the urine flow path and a urinary catheter (catheter) 102 at a distal end of the urine flow path. A first drainage tube 104 extends between the catheter 102 and an interim collection container 132, and a second drainage tube 106 extends between the interim collection container 132 and the container 110. During use, urine flows from the catheter 102 along the first drainage tube 104 to the interim collection container 132. The urine further flows from the interim collection container 132 along the second drainage tube 106 to the container 110.

The interim collection container 132 is configured for deployment adjacent (or in close proximity to) the patient such as between the patient's legs, for example. The first drainage tube 104 is sized to extend a short distance between the catheter 102 and the interim collection container 132. The short length of the first drainage tube 104 facilitates the prevention of the urine stagnating within the first drainage tube 104 (e.g., within a dependent loop of the first drainage tube 104) which in some instances may block or inhibit urine flow along the first drainage tube 104. As such, the first drainage tube 104 may define a length between about 6 inches and 24 inches. The first drainage tube 104 may be extruded of a semi-rigid plastic, such as a PVC, for example, that resists crushing by the patient or kinking during use.

The container 110 is configured for placement at the side of the patient's bed 191. As such, the second drainage tube 106 may define a length sufficient to extend from the interim collection container 132 which may be located between the patient's legs and the container 110 located at the side of the bed 191. The first and second drainage tubes 104, 106 may be fixedly attached to the interim collection container 132. The first drainage tube 104 may be extruded of a semi-rigid plastic, such as a PVC, for example, that resists crushing by the patient or kinking during use.

The container 110 includes a container portion 110A and a cap portion 110B. The cap portion 110B may be located at the top of the container 110 during use. The cap portion 110B may be removably attached to the container portion 110A so that a clinician may remove the cap portion 110B to empty the urine from the container 110 or otherwise access the urine within the container 110. The container 110 may be formed of a rigid material, such as a rigid plastic, for example so that the container 110 does not collapse when a vacuum is applied to the container 110. The container 110 may define capacity consistent with a volume of urine typically excreted by the patient over a defined time period, such as an 8, 12, or 24 hour time period, for example.

The interim collection container 132 may also be formed of a rigid material (e.g., a rigid plastic) so that the interim container 132 does not collapse during use, such as when the patient exerts a crushing force onto the interim container 132. In some embodiments, the interim collection container 132 may include a semi-rigid container or may include a fluid collection bag having a wire frame. In some embodiments, the wire frame may include an internal skeleton or an external wire frame. The interim collection container 132 may define a capacity that is less than the capacity of the container 110. For example, the interim collection container 132 may define a capacity that is about 1 L or less.

The scale 140 is configured to operatively couple with the container 110 during use so that the scale 140 may obtain a weight of the container 110 including the urine collected therein. The scale 140 may be coupled with a frame 120 where the frame 120 is attached to the bed 191. The scale 140 may be coupled between the frame 120 and the container 110 via any suitable fashion such that the weight of the container 110 may be determined by the scale 140. For example, in the illustrated embodiment, the scale 140 may be placed on top of a base of the frame 120 and the container 110 is placed on top of the scale 140.

The system module 150 is coupled with the scale 140 so that the system module 150 may receive weight signals/data from the scale 140. In some embodiments, the system module 150 may be coupled with scale 140 via a wired connection. In other embodiments, the scale 140 may be a smart scale capable of wirelessly communicating with the system module 150. The system module 150 may be coupled with the bed 191, such as hung on a bed rail, for example. In other embodiments, the system module 150 may be located separate from the bed 191, such as on a countertop, for example. In still other embodiments, the system module 150 may be a portable device, such as a tablet, for example.

The system 100 further includes a module 150 having a module console 152. In some embodiments, the module console 152 may be coupled to the display 150A. In some embodiments, the module console 152 may be a separate structure from the display 150A. The display 150A may be configured to project thereon, one or more urine volume measurements or other data pertain to urine output as will be described in more detail herein. The scale 140 is in communication with the module console 152. In some embodiments, the module 150 may be configured to be detachably coupled to the frame 120. In an embodiment, the module console 152 may be physically coupled to the scale 140. In an embodiment, the scale 140 may include a user interface (not shown) configured to display scale related information or data.

The pump 131 is configured to draw air from the container 110. The pump 131 is fluidly coupled with the container 110 via an air hose 133. During operation, the pump 131 draws air from the container 110 to define a vacuum within the container 110. The pump 131 may be a simple pump having activated/deactivated configurations defined by a switch of the pump 131. In some embodiments, the pump 131 may be activated ("on") continuously during use of the system 100. In other embodiments, the pump 131 may be coupled with system module 150 so that logic of the system module 150 may activate and deactivate the pump 131. In still other embodiments, the pump 131 may be a smart pump wirelessly coupled with system module 150 so that logic of the system module 150 may wirelessly activate and deactivate the pump 131. During use, the vacuum within the container 110 as defined by the pump 131 draws urine proximally along the second drainage tube 106 from the interim collection container 132 to the container 110, thereby transporting the urine from the interim collection container 132 to the container 110. The pump 131 may be spaced away from the container 110 a sizable distance (e.g., several feet). As such, the air hose 133 may define a length of several feet (e.g., 10, 20, 30 or more feet). In some embodiments, the pump 131 may be configured for attachment to a wall.

Figure 2:
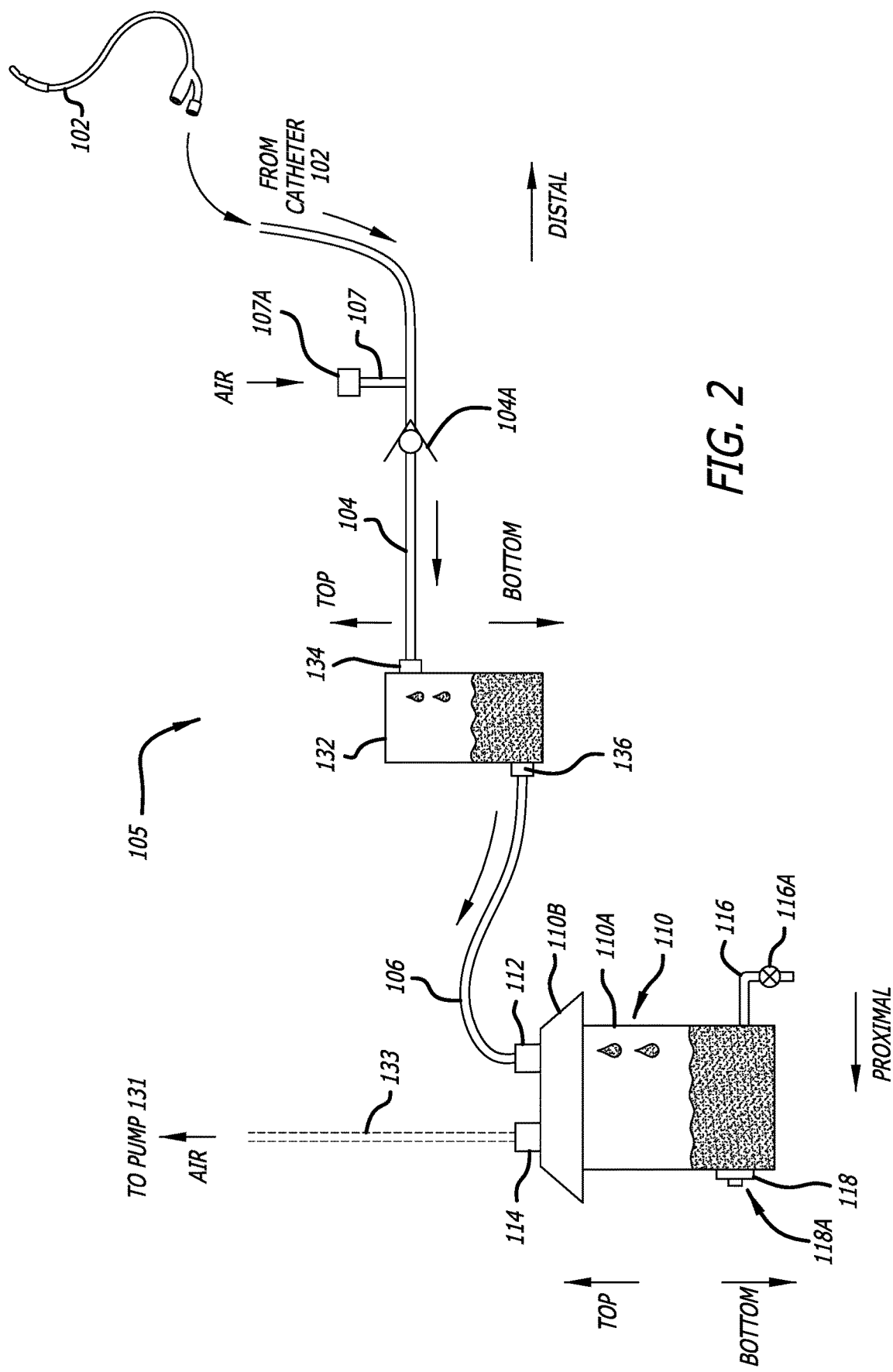
FIG. 2 illustrates a fluid schematic illustration of the urine collection assembly of the system of FIG. 1, in accordance with some embodiments.

FIG. 2 is a hydraulic schematic illustration of the urine collection assembly 105 according to some embodiments. The interim collection container 132 includes an inlet port 134 and an outlet port 136. The inlet port 134 is coupled to a proximal end of first drainage tube 104 and in use the distal end of the first drainage tube 104 is coupled to the urinary catheter 102. In some embodiments, the outlet port 136 is coupled to a proximal end of a second drainage tube 106 and the distal end of the second drainage tube 106 is coupled to a urine intake port 112 of the container 110. In some embodiments, the length of first drainage tube 104 may be relatively short in length to reduce tubing dependent loops in the first drainage tube 104.

The first drainage tube 104 includes air vent 107 (e.g., a side port) in fluid communication with the lumen of the first drainage tube 104. The air vent 107 is generally configured to allow air to enter the lumen of the first drainage tube 104 when a vacuum is present within the first drainage tube 104. During use, urine flows along the first drainage tube 104 from the catheter 102 to the air vent 107 due to gravity. The urine then flows along the first drainage tube 104 from the air vent 107 to the interim collection container 132 due to gravity and/or due to a vacuum with interim collection container 132. The air vent 107 may further be configured to prevent the vacuum within the interim collection container 132 from reaching and potentially cause harm to the patient. In some embodiments, the air vent 107 may be located adjacent the distal end of the first drainage tube 104 to inhibit stagnant urine from accumulating within the first drainage tube 104 up stream of the air vent 107.

The air vent 107 may include a filter 107A in line with the air vent 107 so that air passing through the air vent 107 passes through the filter 107A. The filter 107A may be configured (e.g., include pore size less then 0.2 microns) to maintain a sterile environment within the first drainage tube 104, i.e., prevent microbial ingress. In some embodiments, the filter 107A may be hydrophobic (e.g., include a hydrophobic membrane). In such embodiments, the filter 107A may prevent passage of a urine through the air vent 107, i.e., prevent urine from leaking out of the first drainage tube 104 via the air vent 107. In some embodiments, the filter 107A may be omitted.

The first drainage tube 104 may include a check valve 104A disposed in line therewith. The check valve 104A may be oriented to prevent fluid flow in the distal direction (i.e., toward the catheter 102) along the first drainage tube 104. The check valve 104A may isolate the patient from any positive pressure that may be present (e.g., inadvertently induced) within the first drainage tube 104. In some embodiments, the check valve 104A may be omitted.

The interim collection container 132 is generally configured to receive fluid (e.g., air, urine, or both) flow from the first drainage tube 104 via the inlet port 134 and allow fluid (e.g., air, urine, or both) to exit the interim collection container 132 via the outlet port 136. The outlet port 136 may be positioned at the bottom of the interim collection container 132 so that a substantial entirety of urine collected within the interim collection container 132 may exit via the outlet port 136.

The container 110 includes a urine intake port 112 and an air outlet port 114. In some embodiments, one or both of the urine intake port 112 and the air outlet port 114 may be incorporated into the cap portion 110B. The urine intake port 112 may provide for selective coupling and decoupling of the second draining tube 106 to and from container 110. Similarly, the air outlet port 114 may provide for selective coupling and decoupling of the air hose 133 to and from the container 110. Detaching the second draining tube 106 and the air hose 133 may enable the clinician to transport the container 110 having urine disposed therein away from the patient for analysis or sampling of the urine and/or emptying urine from the container 110. In some embodiments, the cap portion 110B may be coupled to the container portion 110A via a snap fit, a press fit, a twist fit, or an interference fit.

The container 110 may include a drain port 116 configured to allow the clinician to drain urine from the container 110. The drain port 116 may include a valve 116A in line with the drain port 116 to selectively allow and prevent flow urine through the drain port 116. The drain port 116 may enable the clinician to drain urine from the container 110 without detaching the cap portion 110B from the container portion 110A. In some embodiments, the drain port 116 may enable the clinician to drain urine from the container 110 without removing the container 110 from the scale 140. In some embodiments, the drain port 116 may be omitted.

The urine collection assembly 105 may include a sample port 118 configured to allow the clinician to obtain a sample of urine. In the illustrated embodiment, the same port 118 is physically coupled with the container 110. In other embodiments, the sample port 118 may be physically coupled with the first drainage tube 104, the second drainage tube 106, or the interim collection container 132. The sample port 118 may include a valve 118A configured to (i) transition from a closed state to an opened state upon connection of a sampling device (e.g., a syringe) thereto and (ii) transition from the opened state to closed state upon disconnection of the sampling device therefrom. In some embodiments, the sample port 118 may be omitted.

In some embodiments, the interim collection container 132 may be omitted from the urine collection assembly 105. In such embodiments, the first drainage tube 104 is coupled directly to the container 110 and vacuum within the container 110 (as defined by the pump 131) may draw urine distally along the first drainage tube 104 between the air vent 107 and the container 110. In some embodiments, the pump 131 may be continuously activated.

Figure 3A:
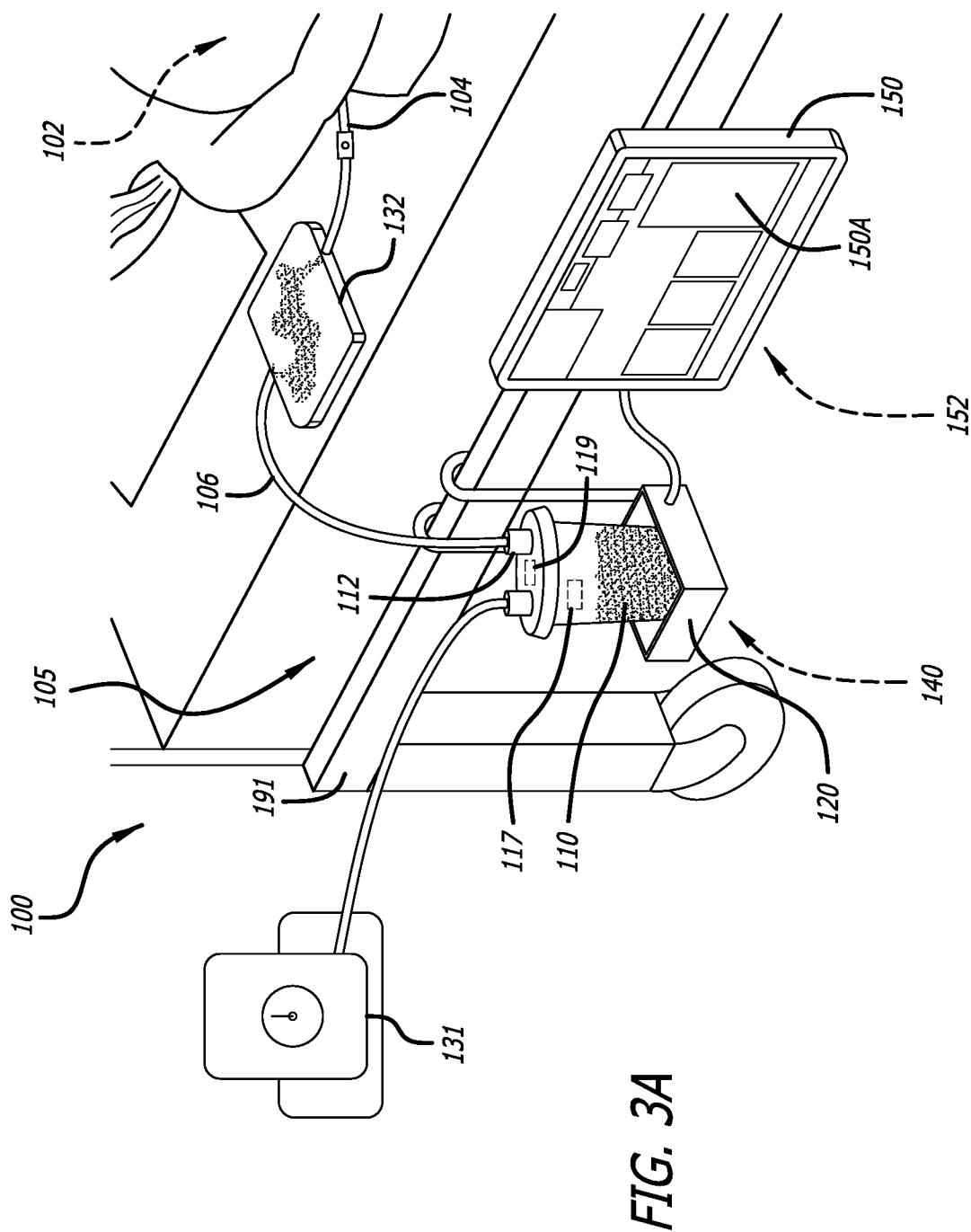
FIG. 3A is a perspective view of system of FIG. 1 illustrating additional components and features, in accordance with some embodiments.

FIG. 3A is a perspective view of the system 100 further illustrating components and features of the system 100, according to some embodiments. In some embodiments, the container 110 may be placed upon the scale 140 and may be stabilized by the frame 120. In some embodiments, as the urine is actively drained into the container 110, the scale 140 may detect the weight of the container 110 including the urine therein. The scale 140 may be configured to generate weight data composed of one or more weight values. The scale 140 may be configured to transmit the weight data to the module console 152 and the module console 152 may be configured to depict the weight data (one or more weight values or volume values) on the display 150A.

In some embodiments, the container 110 may include one or more sensors 119 configured to detect a pressure within the container 110 and/or a fluid level within the container 110. In some embodiments, the one or more sensors 119 may include pressure sensors that are positioned so as to determine a pressure of the urine at the bottom of the container 110, where the pressure of the urine is related to a depth of the urine within the container 110, and where a volume of the urine may be calculated from the depth. In some embodiments, the pressure sensors 119 may be configured to indicate a vacuum within the container 110. In some embodiments, the one or more sensors 119 may include ultrasound emitters, ultrasound sensors, capacitive sensors, or the like to indicate a liquid level of the urine within the container 110, where a volume of the urine may be calculated from the liquid level.

In some embodiments, the urine collection assembly 105 may include an identification device 117, such as a barcode, or an RFID tag, for example. The identification device 117 may include information pertaining to one or more components of the urine collection assembly 105, such as a capacity of the container 110 or the interim collection container 132, for example. For example, the information may include a model identification or serial number of the urine collection assembly 105. In some embodiments, the clinician may scan or otherwise obtain the information from the identification device 117. In some embodiments, the system 100 may link the information to an identification of the patient.

Figure 3B:
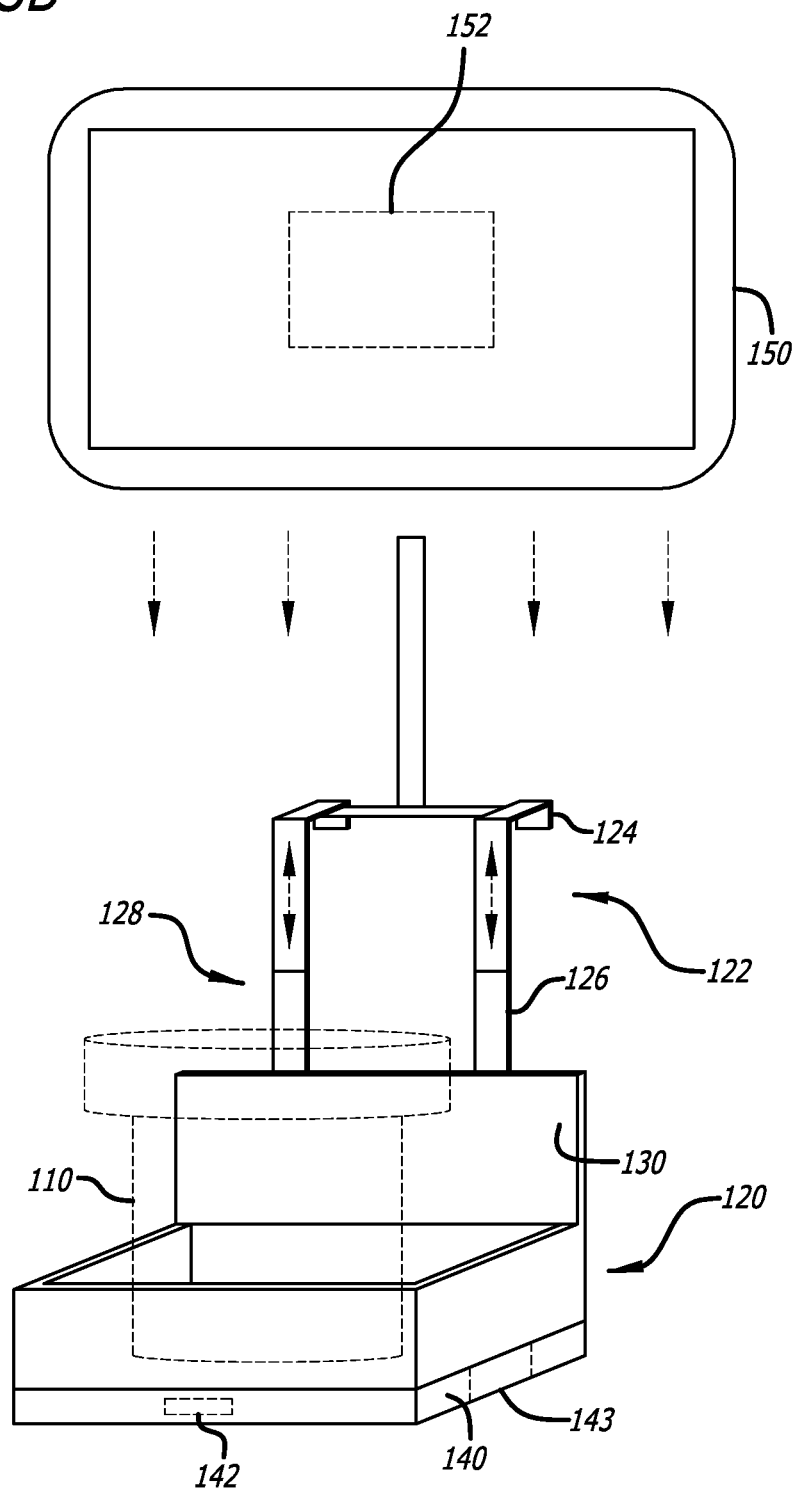
FIG. 3B illustrates a perspective view of the frame including the scale of the system of FIG. 1, in accordance with some embodiments.

FIG. 3B illustrates a perspective view of the frame 120 including the scale 140 and the module 150, in accordance with some embodiments. In some embodiments, the frame 120 may include a coupling mechanism 122 configured to couple the frame 120 to the hospital bed, or other object, such as an IV stand, for example. In some embodiments, the coupling mechanism 122 may include one or more hooks 124 coupled to one or more arms 126 configured to suspend the frame 120 from the hospital bed 191. In some embodiments, the coupling mechanism 122 may include one or more latches (not shown) where the latches are configured to prevent inadvertent decoupling of the frame 120 from the hospital bed 191. In some embodiments, the coupling mechanism 122 may be configured to ensure the frame 120 is level so that the scale 140 may obtain an accurate measurement. In some embodiments, the one or more arms 126 may include length adjustable portions 128, configured to enable a length of each arm 126 to be adjusted to establish a level orientation of the scale 140.

In some embodiments, the scale 140 may include a gyroscope 143 configured to determine the orientation of the scale 140 which may include indicating to the clinician that the scale 140 is or is not level. In some embodiments, the scale 140 may apply a correction factor to the weight data when the gyroscope 143 determines that the scale 140 is not level.

The frame 120 may include one or more walls 130 configured to secure the container 110 within the frame 120. In some embodiments, the walls 130 may transversely extend the length of the container 110. In some embodiments, may define a circumferential perimeter of the frame 120 forming a cavity within which the container 110 may be placed during use.

In some embodiments, the scale 140 may be a smart scale configured to wirelessly communicate with the module console 152. As such, the scale 140 may include a scale console 142 having a wireless communication module. In some embodiments, the scale console 142 may be configured to transmit the weight data from the scale 140 to the module console 152. In some embodiments, the scale console 142 may be in communication with gyroscope 143 and configured to receive gyroscope values from the gyroscope 143.

In some embodiments, the module 150 may be configured to be detachably coupled to the frame 120. The module 150 may be detachably coupled to the frame 120 in a press fit, a snap fit, an interference fit or the like.

Figure 4:
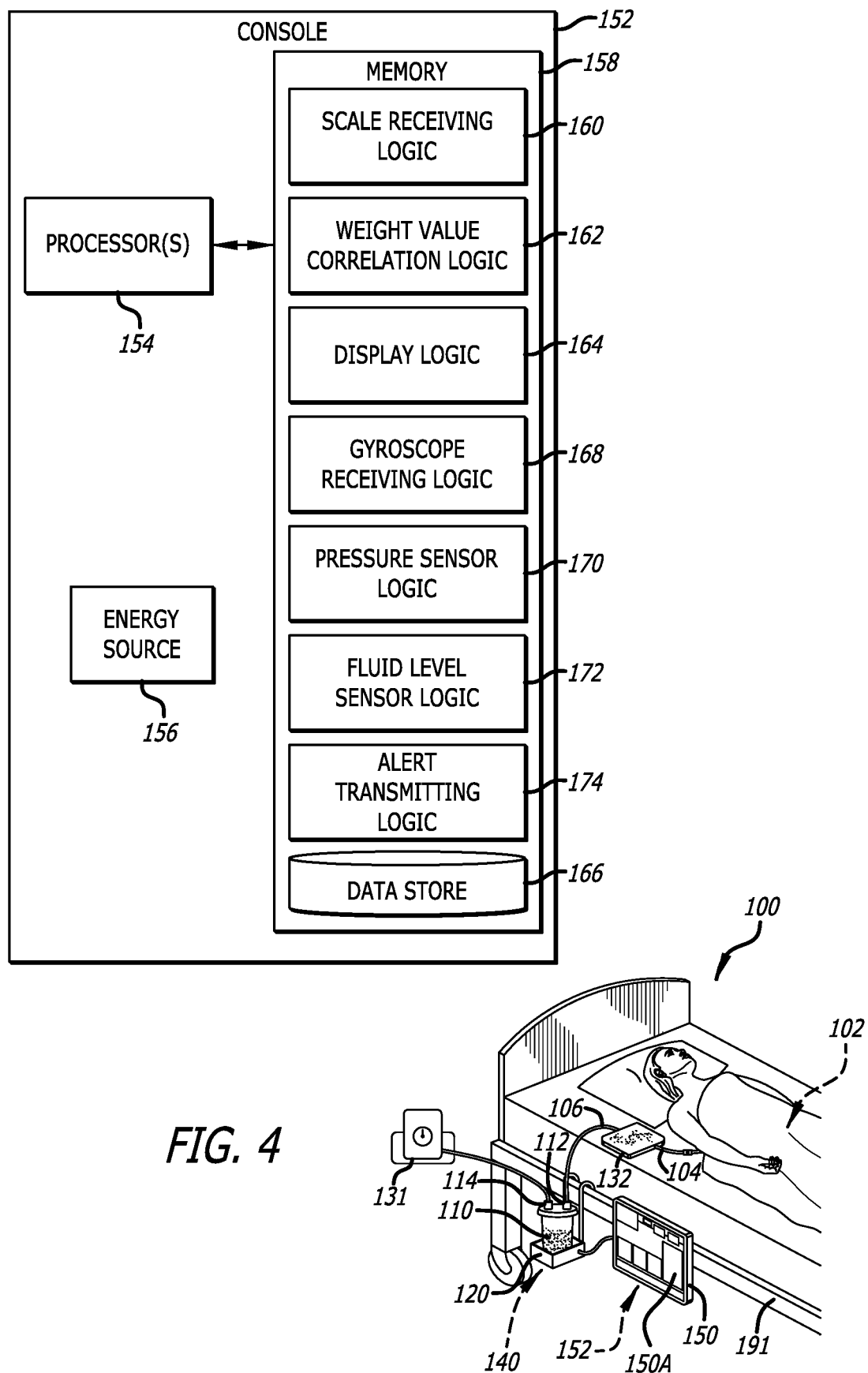
FIG. 4 illustrates a block diagram of some components of the system of FIG. 1 including the console, in accordance with some embodiments.

FIG. 4 illustrates a block diagram of some components of the system 100 including the module console 152, in accordance with some embodiments. In some embodiments, the module console 152 includes one or more processors 154, an energy source 156, non-transitory computer readable medium ("memory") 158, and a number of logic modules. In some embodiments, the module console 152 may be in wireless communication with an electronic medical records system, an external computer device, or both. The module console 152 may transmit information from the module console 152 to the electronic medical records system or an external computer device. In some embodiments, the energy source 156 may include an external power source or rechargeable battery. In some embodiments, wherein the scale 140 is wired to the module console 152, the energy source 156 may be configured to provide power to the scale 140 and to the module 150. For description purposes, the logic modules may include a scale receiving logic 160, a weight value correlation logic 162, a display logic 164, and a data store 166. Optionally, when the scale 140 includes a gyroscope 143 and the container 110 includes the one or more sensors 119, the plurality of logic modules may further include a gyroscope receiving logic 168, a pressure sensor logic 170, a fluid level sensor logic 172, and/or an alert logic 174. In some embodiments, the scale receiving logic 160 may be configured to receive weight data from the scale 140. In some embodiments, the scale 140 may be configured to perform a scale calibration process and the scale receiving logic 160 may be configured to receive confirmation from the scale 140 that the scale 140 has been calibrated.

In some embodiments, the weight value correlation logic 162 may be configured to correlate each weight value with a volume of urine within the container 110. In some embodiments, the weight value correlation logic 162 may also correlate each weight value with a time of day value, i.e., link the weight value corresponding to the time of day the weight value was obtained. In some embodiments, the display logic 164 may be configured to transmit the volume value and time of day value to the display 150A. In some embodiments, the display logic 164 may be configured to transmit the weight value, the volume value, and the time of day value to the electronic medical record system or the external computing device. In some embodiments, the data store 166 may be configured to store each of the weight value, volume value, and/or time of day value.

In some embodiments, the gyroscope receiving logic 168 may be configured to receive the gyroscope values from the scale console 142. In some embodiments, the gyroscope receiving logic 168 may be configured to transmit the gyroscope values to the module 150 to indicate to the user when the scale 140 is or is not level and/or apply a correction factor to the weight data (weight values). In some embodiments, the pressure sensor logic 170 may be configured to receive one or more pressure values from the one or more sensors 119 coupled to the container 110 and in some embodiments, the pressure sensor logic 170 calculate the volumes of the urine based on the pressure values. In some embodiments, the fluid level sensor logic 172 may be configured to receive one or more liquid level values from the one or more sensors 119 and in some embodiments, the fluid level sensor logic 172 calculate the volumes of the urine based on the fluid level values. In some embodiments, the alert logic 174 may be configured to transmit an alert to the display 150A, the external computing device, or the electronic medical record system whenever the pressure within the container 110 falls outside of a pre-determined or user defined threshold. In some embodiments, the alert logic 174 may be configured to transmit an alert to the module 150 whenever the urine volume within the container 110 reaches a pre-determined or user defined level, such as a capacity of the container 110, for example.

Figure 5A:
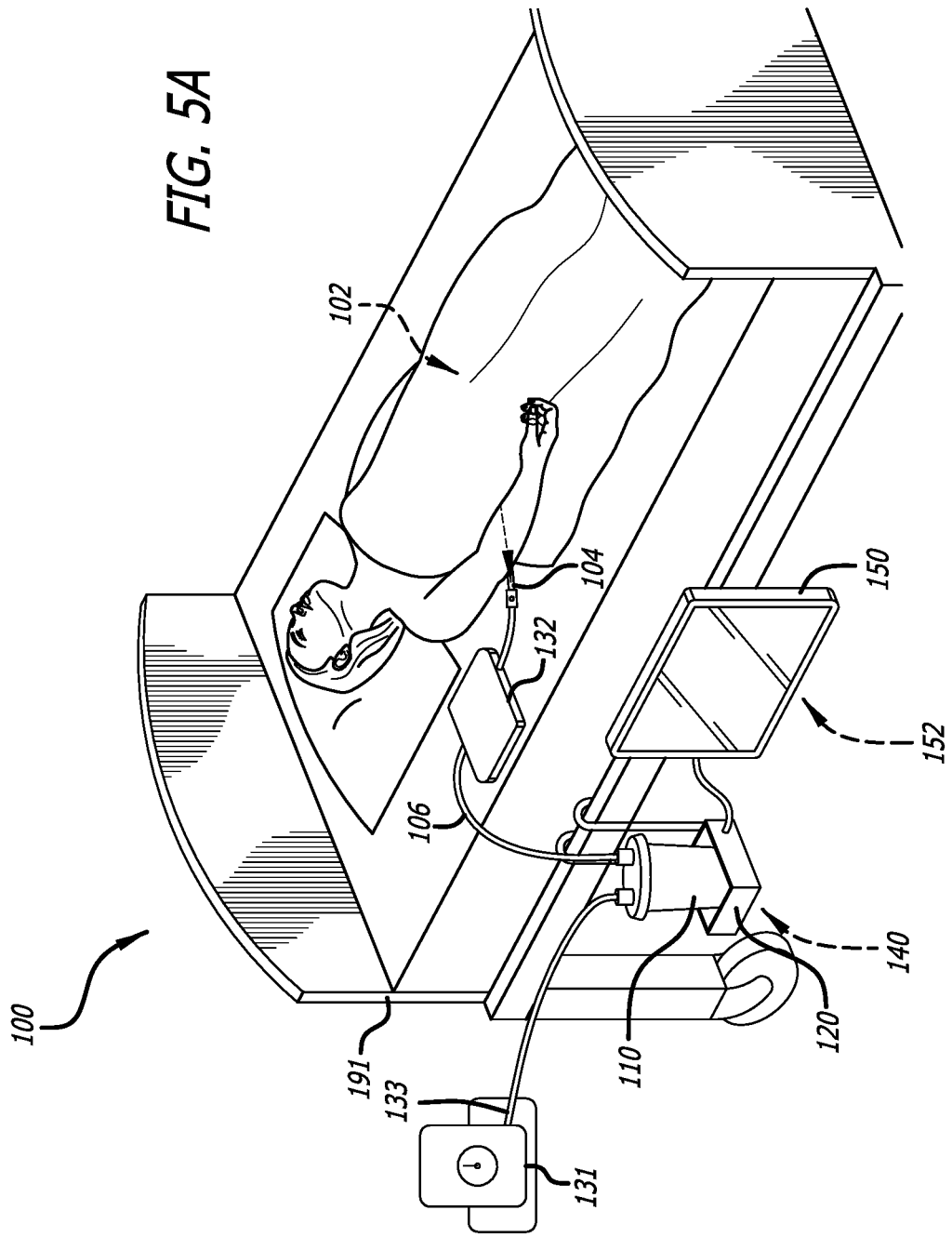
Figure 5B:
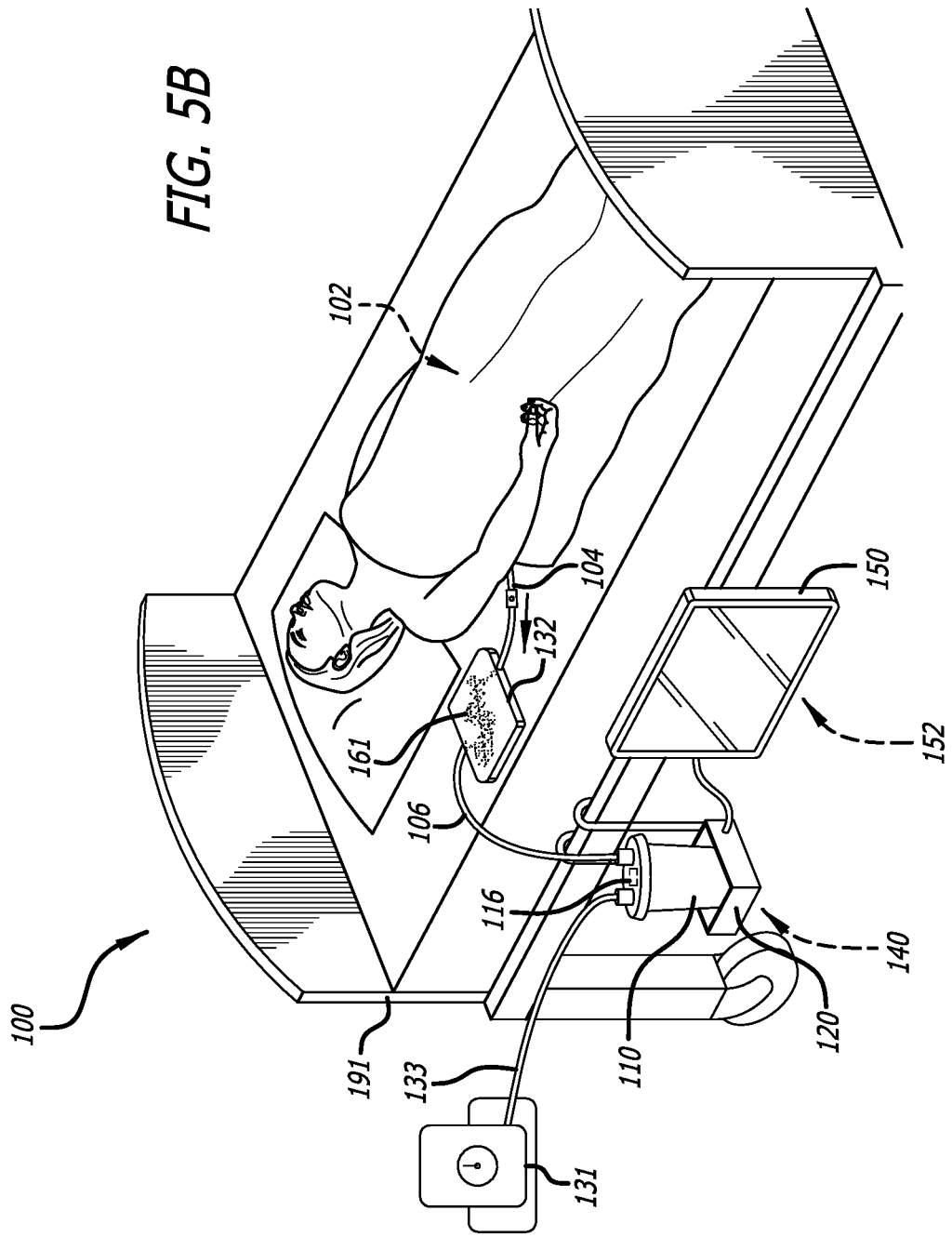

FIGS. 5A-5C illustrate the system 100 in various states of a collecting urine output from a patient. FIG. 5A illustrates the system 100 coupled with the patient prior to patient excreting urine via the urinary catheter 102. The urinary catheter 102 is in fluid communication with the container 110 with the interim collection container 132 disposed therebetween. The frame 120 is coupled to the hospital bed 191. The scale 140 is coupled with the frame 120 and the container 110 is placed on the scale 140. For illustrative purposes, the interim collection container 132 is shown placed on the hospital bed 191. The pump 131 is coupled with the container 110 via the air hose 133. The pump 131 is in the deactivated state. The interim collection container 132 and the container 110 are empty of urine.

FIG. 5B depicts a second state of collecting urine output where the patient has excreted a first urine volume 161 via the urinary catheter 102. As such, the first urine volume 161 is shown disposed within the interim collection container 132 having flowed through the first drainage tube 104 due to gravity. The pump 131 remains in the deactivated state and the container 110 remains empty of urine.

FIG. 5C depicts a third state of collecting urine output after the patient has excreted a first urine amount 161 via the urinary catheter 102. In the third state, the pump 131 is activated so as to draw air from the container 110 defining a vacuum within the container 110. The vacuum within the container 110 has drawn the first urine amount 161 from the interim collection container 132 along the second drainage tube 106 into the container 110 while air is drawn into the air vent 107. As such, the first urine amount 161 is shown disposed within the container 110. The interim collection container 132 is void of the first urine amount 161 and ready to deceive a second urine amount. Upon collection of the first urine amount 161 within the container 110, the pump 131 may be deactivated. With the first urine amount 161 collected within the container 110, the scale 140 may obtain a weight of the first urine amount 161.

The second and third states illustrated by FIGS. 5B, 5C, respectively may be repeated multiple times while collecting urine output from the patient. In some implementations, the pump 131 may be continuously activated.

FIG. 6 illustrates a flow chart of an exemplary method 200 of measuring (or otherwise determining) a volume urine output from a patient, in accordance with some embodiments. In some embodiments, the method 200 includes coupling the urine collection assembly to the patient (block 202). In some embodiments, coupling the urine collection assembly to the patient includes coupling the urine collection assembly to a urinary catheter. In some embodiments, the coupling the urine collection assembly to the patient includes placing the interim collection container on the bed adjacent the patient. In some embodiments, the coupling the urine collection assembly to the patient placing the interim collection container between the legs of the patient.

The method 200 further includes establishing a flow urine from the patient to the interim collection container via the first drainage tube (block 204). In some embodiments, establishing a flow urine from the patient to the interim collection container may include catheterizing the patient. In some embodiments, the establishing a flow urine from the patient to the interim collection container includes collecting the urine within the interim collection container. In some embodiments, collecting the urine within the interim collection container includes collecting a first amount of the urine within the interim collection container and subsequently, collecting a second amount of the urine within the interim collection container.

The method 200 further includes drawing the urine from the interim collection container to a final collection container (block 206). Drawing the urine from the interim collection container to the final collection container includes drawing air into the air vent of the first drainage tube where a pressure (e.g., atmospheric pressure) of the air transports the urine along the second drainage tube from the interim collection container to the final collection container. In some embodiments, the air vent includes a filter that ensures the air passing through the air vent is sterile. In some embodiments, drawing air into the first drainage tube includes activating a vacuum pump coupled with the final collection container to generate a vacuum within the final collection container.

In some embodiments, drawing the urine from the interim collection container to the final collection container includes drawing the first amount of the urine from the interim collection container to the final collection container and subsequently, drawing the second amount of the urine from the interim collection container to the final collection container. In some embodiments, activating the vacuum pump includes (i) activating the vacuum pump for a first activation time period to transport the first amount of urine from the interim collection container to the final collection container, (ii) deactivating the vacuum pump for a defined deactivation time period after the first activation time period, and (iii) activating the vacuum pump for a second activation time period after the defined deactivation time period to transport the second amount of urine from the interim collection container to the final collection container The method 200 further includes measuring (or otherwise determining) the weight of the urine within the final collection container (block 208). Measuring the weight may include placing the final collection container on a scale where the scale is attached to a frame and the frame is suspended from a bed rail. In some embodiments, measuring the weight may include adjusting an orientation of the frame so that the scale is horizontal. In some embodiments, measuring the weight of the urine includes measuring the weight of the first amount of the urine collected within the final collection container and subsequently, measuring the weight of the second amount of the urine collected within the final collection container. In some embodiments, measuring the weight may include calculating a volume of the urine within the final collection container based on the weight. In some embodiments, measuring the weight may include correlating the measuring of the weight with a time of day.

In some embodiments, determining the weight of urine includes determining a rate of urine output. In some embodiments, the determining a rate of urine output may be based on the weight of the second amount of urine and the defined deactivation time period. For example, the rate of urine output may be determined by dividing the weight of the second amount of urine by the defined deactivation time period to calculate the rate of urine output by weight. Determining a rate of urine output may also include converting the rate of urine output by weight to a rate of urine output by volume.

The method 200 further includes depicting the volume of the urine collected within the final collection container on the display (block 210). In some embodiments, depicting the volume may include calculating the volume of the urine within the final collection container based on the weight. In some embodiments, depicting the volume may include correlating the volume of urine within the final collection container with a time of day. In some embodiments, depicting the volume may include depicting the rate of the urine output.

The method 200 further includes transmitting the volume of urine within the final collection container to the an external computing device (block 212). In some embodiments, transmitting the volume includes transmitting the time of day correlated with the volume. In some embodiments, transmitting the volume includes transmitting the rate of urine output. In some embodiments, the external computing device may be coupled with (or a component of) an electronic medical record system.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. An automated urinary output monitoring system for determining a urine output from a patient supported by a bed surface, comprising:
    a urine collection assembly comprising:
        a urinary catheter, a distal tip thereof configured to pass through an insertion site to be disposed inside the patient;
        an interim collection container in fluid communication with the urinary catheter by way of a first drainage tube and configured to be placed adjacent the insertion site on the bed surface, the interim collection container defining a height from the bed surface that is less than 10% of a width or a length of the interim collection container to facilitate positioning a fluid surface disposed within the interim collection container below the insertion site, the interim collection container configured to prevent collapse when a crushing force is applied; and
        a final collection container formed of a rigid material and fluidly coupled with the interim collection container via a second drainage tube;
    a scale console comprising:
        a frame configured to be coupled to a bed rail of the patient and defining a shelf to support a lower-most surface of the final collection container disposed thereon;
        a scale disposed between the final collection container and the shelf and configured to determine a change in weight of the final collection container; and
        one or more processors and non-transitory computer readable medium having logic stored thereon that, when executed by the one or more processors, performs scale operations including:
            i) receiving weight data from the scale;
            ii) determining a volume of urine collected within the final collection container; and
            iii) wirelessly communicating the volume of urine to a system module; and
    a pump configured to draw air from an outlet port disposed in a top-most surface of the final collection container and cause urine to flow from the interim collection container to the final collection container via the second drainage tube.

2. The system according to claim 1, wherein the pump is fluidly coupled with the final collection container via an air hose.

3. The system according to claim 2, wherein the pump is configured to generate vacuum within the final collection container.

4. The system according to claim 1, wherein the urine collection assembly includes an air vent coupled with the first drainage tube, the air vent configured to enable air to flow from an environment into a lumen of the first drainage tube.

5. The system according to claim 4, wherein the air vent is configured to prevent urine from flowing from the lumen to the environment.

6. The system according to claim 4, wherein the air vent includes a filter disposed in line with the air vent, the filter configured to prevent microbial contaminates from entering the lumen via the air vent.

7. The system according to claim 1, wherein the first drainage tube includes a one-way valve disposed in line with the first drainage tube, the one-way valve configured to prevent fluid flow along the first drainage tube toward the urinary catheter.

8. The system according to claim 1, wherein the urine collection assembly includes the urinary catheter coupled with the first drainage tube.

9. The system according to claim 1, wherein the frame further includes one or more length-adjustable arms configured to maintain the scale in a level orientation.

10. The system according to claim 9, wherein the frame includes one or more hooks configured to suspend the frame from the bed rail.

11. The system according to claim 1, further comprising the system module wirelessly coupled with the scale console and the pump, and including a touch-screen display, the system module including one or more processors and non-transitory computer readable medium having logic stored thereon that, when executed performs system operations, including:
wirelessly receiving volume data from the scale console; and
depicting the volume of urine on the touch-screen display.

12. The system according to claim 11, wherein:
the final collection container includes a pressure sensor, and the system operations further include:
receiving pressure data from the pressure sensor; and
at least one of (i) determining a depth of the urine contained within the final collection container based on the pressure data and calculating the volume of urine based on the depth or (ii) detecting a vacuum within the final collection container.

13. The system according to claim 11, wherein the system operations further include transmitting the volume of the urine to at least one of (i) an electronic medical record system or (ii) an external computing device.

14. The system according to claim 1, wherein:
the scale console further includes a gyroscope, and the scale operations further include:
receiving gyroscope data from the gyroscope;
determining an orientation of the scale based on the gyroscope data; and
at least one of (i) communicating the orientation of the scale to the system module or (ii) applying a correction factor to weight data based on the orientation of the scale.

15. The system according to claim 1, wherein the crushing force includes a radially inward force applied to an outer surface of the interim collection container.

16. The system according to claim 1, wherein the crushing force includes a vacuum force applied to an interior of the interim collection container.

17. The system according to claim 1, wherein the interim collection container is configured to be placed adjacent the patient and the first drainage tube is between 6 and 24 inches to mitigate formation of dependent loops therein.

18. The system according to claim 1, wherein the system module is a handheld tablet and configured to be releasably attached to the bed rail.

19. A method of measuring a volume of urine output from a patient supported by a surface, comprising:
receiving urine from a urinary catheter via a first drainage tube, the urinary catheter entering the patient at an insertion site, the first drainage tube extending between the urinary catheter and an interim collection container configured to prevent collapse when a crushing force is applied;
collecting the urine within the interim collection container placed adjacent the insertion site on the surface, the interim collection container defining a height from the surface that is less than 10% of a width or a length of the interim collection container to facilitate positioning a fluid surface disposed within the interim collection container below the insertion site;
forming a vacuum within a final collection container that is formed of a rigid material;
drawing air into the first drainage tube via an air vent of the first drainage tube, a pressure of the air transporting the urine from the interim collection container to the final collection container;
determining a weight of the urine within the final collection container by a scale supported by a shelf of a frame coupled to a bed rail of the patient, the scale disposed between a lower-most surface of the final collection container and the shelf;
calculating the volume of the urine within the final collection container based on the weight; and
wirelessly communicating the volume of urine to a handheld system module.

20. The method according to claim 19, wherein drawing air into the first drainage tube includes generating a vacuum within the final collection container.

21. The method according to claim 19, wherein:
collecting the urine within the interim collection container includes:
collecting a first amount of urine; and
collecting a second amount of urine subsequent to collecting the first amount of urine; and
drawing air into the first drainage tube includes:
activating a vacuum pump coupled with the final collection container for a first activation time period to transport the first amount of urine from the interim collection container to the final collection container;
deactivating the vacuum pump for a defined deactivation time period after the first activation time period; and
activating the vacuum pump for a second activation time period after the defined deactivation time period to transport the second amount of urine from the interim collection container to the final collection container.

22. The method according to claim 21, wherein determining the weight of the urine within the final collection container includes:
determining a weight of the first amount of urine, and
determining a weight of the second amount of urine.

23. The method according to claim 22, further comprising determining a rate of urine output based on the weight of the second amount of urine and the defined deactivation time period.

24. The method according to claim 19, wherein the crushing force includes a radially inward force applied to an outer surface of the interim collection container.

25. The method according to claim 19, wherein the crushing force includes a vacuum force applied to an interior of the interim collection container.

26. The method according to claim 19, wherein the interim collection container is configured to be placed adjacent the patient and the first drainage tube is between 6 and 24 inches to mitigate formation of dependent loops therein.

\* \* \* \* \*